(12) United States Patent
Kim

(10) Patent No.: US 9,215,864 B2
(45) Date of Patent: Dec. 22, 2015

(54) METHOD OF PRODUCING EARTHWORM CASTINGS USING SOLID FUEL ASH AND EARTHWORM BED FOR PRODUCING EARTHWORM CASTINGS

(76) Inventor: Hyung Ju Kim, Busan (KR)

(*) Notice: Subject to any disclaimer, the term of this patent is extended or adjusted under 35 U.S.C. 154(b) by 445 days.

(21) Appl. No.: 13/518,796

(22) PCT Filed: Aug. 18, 2011

(86) PCT No.: PCT/KR2011/006072
§ 371 (c)(1),
(2), (4) Date: Jun. 22, 2012

(87) PCT Pub. No.: WO2012/026707
PCT Pub. Date: Mar. 1, 2012

(65) Prior Publication Data
US 2012/0318199 A1 Dec. 20, 2012

(30) Foreign Application Priority Data
Aug. 24, 2010 (KR) .......................... 10-2010-0081752

(51) Int. Cl.
*A01K 29/00* (2006.01)
*A01K 67/033* (2006.01)
(Continued)

(52) U.S. Cl.
CPC ............. *A01K 67/0332* (2013.01); *C05F 1/005* (2013.01); *C05F 17/0045* (2013.01)

(58) Field of Classification Search
CPC ... A01N 63/00; A01N 2300/00; A01N 25/34; A01N 43/12; A01N 43/90; A01N 25/08; A01N 25/26; A01N 43/08; A01N 41/02; A01N 43/36; A01N 43/38; A01N 43/54; A01N 43/56; A01N 43/58; A01N 47/06

USPC .............................................. 119/6.7, 6.5, 6
See application file for complete search history.

(56) References Cited

U.S. PATENT DOCUMENTS 3,654,903 A * 4/1972 Montgomery ................. 119/6.7
3,961,603 A * 6/1976 Gaddie, Sr. .................... 119/6.7
(Continued)

FOREIGN PATENT DOCUMENTS

KR 100262149 4/2000
KR 100283609 12/2000
(Continued)

*Primary Examiner* — Andrea Valenti
(74) *Attorney, Agent, or Firm* — IPLA P.A.; James E. Bame

(57) ABSTRACT

A method of producing earthworm castings by feeding earthworms with feed prepared by mixing solid fuel ash with shells, crab shells and yellow earth and to an earthworm bed for producing earthworm castings, comprises the steps of: grinding solid fuel ash; washing shells and crab shells to remove salt, and then removing 80% or more of water therefrom; grinding the washed shells and crab shells; mixing 60-70 wt % of yellow earth, 20-30 wt % of the solid fuel ash and 10-20 wt % of the ground shells and crab shells; fermenting and maturing the mixture; and feeding the matured mixture to earthworms to allow the earthworms to produce earthworm castings. The earthworm bed (50) comprises: a feeding unit (52) through which feed prepared by mixing solid fuel ash with shells, crab shells and yellow earth is fed; a breeding chamber (51) in which earthworms are bred to produce earthworm castings; and a discharge unit (53) through which the earthworm castings produced in the breeding chamber (51) are discharged. According to the invention, ash from a solid fuel boiler is used as feed for earthworms to produce earthworm castings, whereby problems associated with the disposal of the solid fuel ash are solved in an environmentally friendly and economical manner. The produced earthworm castings are used as fertilizers, solid amendments and the like.

1 Claim, 3 Drawing Sheets

(51) Int. Cl.
*C05F 1/00* (2006.01)
*C05F 17/00* (2006.01)

(56) References Cited

U.S. PATENT DOCUMENTS

| | | | | |
|---|---|---|---|---|
| 4,334,498 | A | * | 6/1982 | Bedding .................. 119/6.7 |
| 4,513,685 | A | * | 4/1985 | Frijters et al. ............. 119/6.7 |
| 7,156,048 | B2 | * | 1/2007 | Olive et al. .............. 119/6.7 |

FOREIGN PATENT DOCUMENTS

| | | | |
|---|---|---|---|
| KR | 20020077740 A | * 10/2002 | .............. C05F 15/00 |
| KR | 1020030032249 | 4/2003 | |
| KR | 1020040063882 | 7/2004 | |
| KR | 20-20058-0000166 | 2/2008 | |
| KR | 100934127 | 12/2009 | |

* cited by examiner

METHOD OF PRODUCING EARTHWORM CASTINGS USING SOLID FUEL ASH AND EARTHWORM BED FOR PRODUCING EARTHWORM CASTINGS

BACKGROUND OF THE INVENTION

The present invention relates to a method of producing earthworm casts using solid fuel ash and an earthworm bed for producing earthworm castings, and more particularly to a method of producing earthworm castings using ash generated from the combustion of solid fuel, the method being able to dispose of the solid fuel ash in an environmentally friendly and economical manner by feeding the solid fuel ash to earthworms to produce earthworm castings, and to an earthworm bed for producing earthworm castings.

Refuse-derived fuels (RDFs; solid fuels) produced from food waste, combustible waste, ocean waste or the like are incinerated to utilize the heat energy. Such solid fuels have a high heating value and are low-priced because they are produced from waste. Moreover, recycling of waste resources for producing the solid fuels results in an economic benefit, and gas generated from the combustion of the solid fuels does not corrode the combustion apparatuses. In addition, a facility for storing the solid fuels does not require a separate safety mechanism. Due to such advantages, the solid fuels are widely used as alternative energy not only in various industrial fields, but also in farming and fishing villages, in order to reduce the use of oil.

An effective method for disposal of ash generated from the combustion of the solid fuels has not yet been developed, and thus the ash is buried in landfills. Thus, the cost for disposal of the ash is required, and environmental pollution is caused by landfilling of the ash. For this reason, technology capable of disposing of the ash is required.

Meanwhile, earthworm castings are excrements of earthworms, which are obtained from the digestion of feed in the digestive tract of the earthworms and contain undegraded fiber residue mixed with viscous materials. Earthworms can produce relatively uniform earthworm castings by mixing even non-uniform feed vertically and in the intestines.

Such earthworm castings have high contents of exchangeable calcium, magnesium, potassium, phosphoric acid and organic matter. In addition, the physical and chemical properties of earthworm castings do not significantly differ between food sources. This is because earthworms use only organic matters having similar humification grades among different feed sources, due to the limited digestive function thereof.

Moreover, earthworm castings are dark brown, do not evolve an unpleasant odor and gas, and contain organic matter, trace elements such as nitrogen, phosphoric acid and potassium, and a large amount of antibiotic *Bacillus* sp. microorganisms which destroy or dissolve mold harmful to soil to increase the resistance of the soil to blight and harmful insects. Thus, earthworm castings are known as the best natural organic fertilizer.

Hereinafter, the production of fertilizers and earthworm castings will be described.

Korean Patent Laid-Open Publication No. 10-2003-0013054 discloses a method for preparing a compound fertilizer, the method comprising the steps of: mixing 100 parts by weight of a sewage sludge dehydrated cake and 28-59 parts by weight of caustic lime, air-drying and curing the mixture for 3-5 days such that the sewage sludge dehydrated cake has a water content of 3-10%; and mixing 100 parts by weight of the dried sewage sludge with 40-60 parts by weight of stainless steel slag and 5-15 parts by weight of a gallium additive.

Korean Patent Laid-Open Publication No. 10-2005-0088843 discloses a method of producing a fertilizer using sewage sludge, the method comprising: mixing 65-70 wt % of sewage sludge, 5-10 wt % of sawdust, 5-10 wt % of rice bran, 5-10 wt % of a crab shell and 5-10 wt % of zeolite; inoculating seed bacteria, cultured in rice bran, into the mixture in an amount of 1 wt % based on the total amount of the mixture; and fermenting the inoculated mixture in a fermenter at an air supply rate of 200 ml/kg·min to obtain a compost, in which the initial fermentation product is turned over when the temperature thereof decreases to about 30~50° C. during the fermentation, and is then composted until the temperature thereof no longer changes.

Korean Patent Registration No. 10-0812686 discloses earthworm castings produced by feeding earthworms with sludge from milk processing, and a method for recycling earthworms. It discloses a method in which sludge from milk processing is composted and recycled in a simple and cost-effective manner compared to conventional sludge treatment methods.

Korean Patent Laid-Open Publication No. 10-2010-0026226 discloses a soil amendment comprising 100 parts by weight of an absorbable polymer resin, 30-70 parts by weight of chitosan, 20-40 parts by weight of a fermentation culture obtained by inoculating a medium with at least one strain selected from the group consisting of *Bacillus subtilis, Lactobacillus*, yeasts and filamentous fungi and culturing the inoculated strain, 20-40 parts by weight of mica, and 20-40 parts by weight of calcium oxide powder.

Hereinafter, earthworm breeding apparatuses for producing earthworm castings will be described.

Korean Patent Laid-Open Publication No. 10-2002-0045871 discloses an apparatus for breeding earthworms using organic waste, comprising: an assembly consisting of an earthworm box, in which earthworms are bred by feeding organic waste, and an earthworm casting box; a storehouse in which the assembly can be received; and a transport means.

Korean Patent Laid-Open Publication No. 10-1998-082831 discloses a method and apparatus of breeding earthworms using food waste and collecting earthworm castings, in which food waste is fed from the top while earthworm castings are collected from the bottom, and earthworm castings, accumulated during the time taken for earthworm eggs to hatch and move, are crushed, discharged and collected, thereby growing earthworms.

Korean Patent Laid-Open Publication No. 10-2000-63722 discloses a grinding device in which an organic raw material stored in a storage tank is finely ground; a separating device in which the material ground in the grinding device is separated according to size and large grains are transferred again to the grinding device; an air blowing device by which the fine organic material separated in the separating device is transferred by blowing air; a drying device in which the organic material transferred by the air blowing device is dried; and a packaging device in which the organic material dried in the drying device is put in a bag having a specific size.

Korean Patent Laid-Open Publication No. 10-2003-0032249 discloses an earthworm breeding apparatus in which an earthworm breeding bed is formed in the shape of a box, such that earthworms can be bred in a three-dimensional multilayer structure and, at the same time, can stably grow, and a surplus of earthworm castings can be easily separated.

Korean Patent Laid-Open Publication No. 10-2004-0006777 discloses an earthworm breeding apparatus for producing earthworm castings, in which earthworms can be bred in a breeding bed in a layered state, whereby the breeding area of the earthworms is maximized and earthworm castings are easily collected using an automated breeding method.

Korean Patent Laid-Open Publication No. 10-2004-0063882 discloses a method for producing earthworm castings, the method comprising: fermenting and aging organic waste such as food waste in a composting process to obtain a fully mature compost; transferring the compost to a band-type earthworm bed having a multistage belt conveyor; breeding earthworms using the transferred compost; sending the bred earthworms to an earthworm separating machine in which mature earthworms are separated; and sending a portion of earthworm castings (for seeding) into the earthworm bed by an earthworm casting return bucket conveyor and sensing the remaining earthworm castings to a packaging process by an earthworm casting transfer conveyor.

Korean Utility Model Registration No. 20-0294434 discloses an earthworm breeding apparatus for producing earthworm castings, in which earthworms can be bred in a breeding bed in a layered state, whereby the breeding area of the earthworms is maximized and earthworm castings are easily collected using an automated method.

Korean Utility Model Registration No. 20-0287400 discloses a device for easily separating earthworms, earthworm eggs and earthworm castings, in which pins capable of separating earthworms are formed to the inside of a cylindrical housing, and holes capable of discharging earthworm castings are formed through the cylindrical housing.

Meanwhile, chitosan can generally be obtained from shells, crab shells and the like. This chitosan can reduce the density of *Fusarium* fungi in soil, can increase the antiviral activity of plants, can promote the proliferation of useful microorganisms (*Actinomycetes*, lactic acid bacteria, etc.) in soil, can increase the activity of chitinase from microorganisms, and can kill or inactivate pathogenic microorganisms in soil.

SUMMARY OF THE INVENTION

It is an object of the present invention to solve the problems associated with the disposal of ash generated from the combustion of solid fuels produced from food waste, combustible waste, ocean waste or the like, by feeding the solid fuel ash to earthworms. Another object of the present invention is to produce good-quality earthworm castings using solid fuel ash by feeding earthworms with a mixture of solid fuel ash, yellow earth, and ocean waste, such as shells or crab shells, which are difficult to dispose of, but have useful components such as chitosan, and to use the earthworm castings in a wide range of applications, including fertilizers, soil amendments and the like.

In order to accomplish the above objects, the present invention provides a method for producing earthworm castings, the method comprising the steps of: grinding solid fuel ash; washing shells and crab shells to remove salt, and then removing 80% or more of water therefrom; grinding the washed shells and crab shells; mixing 60-70 wt % of yellow earth, 20-30 wt % of the solid fuel ash and 10-20 wt % of the ground shells and crab shells; fermenting and maturing the mixture; and feeding the matured mixture to earthworms to allow the earthworms to produce earthworm castings.

The present invention also provides an earthworm bed for producing earthworm castings, comprising: a feeding unit through which feed prepared by mixing solid fuel ash with shells, crab shells and yellow earth is fed; a breeding chamber in which earthworms are bred to produce earthworm castings; and a discharge unit through which the earthworm castings produced in the breeding chamber are discharged.

In the earthworm bed, the breeding chamber has holes formed through the top thereof, feeding pipes which fit into the holes of the breeding chamber are formed to extend from the feeding unit, the feeding unit is detachably coupled to the top of the breeding chamber such that the feed may be fed through the feeding unit; and the discharge unit for discharging the produced earthworm castings is provided at both sides of the breeding chamber and comprises a discharge opening formed through the breeding chamber, and a discharge door coupled to the discharge opening, such that the discharge of the earthworm castings may be performed by opening the discharge door, inserting a discharge scoop into the discharge chamber and discharging the earthworm castings from the breeding chamber.

According to the present invention, ash generated from the combustion of solid fuels is mixed with shells and crab shells, and the mixture is fed to earthworms to produce earthworm castings, whereby problems associated with the disposal of solid fuel ash can be solved in an environmentally friendly and economical manner. In addition, solid fuel ash together with shells and crab shells is used as feed for earthworms to produce earthworm castings, whereby higher-quality fertilizers, soil amendments and the like can be produced.

DETAILED DESCRIPTION OF THE INVENTION

Production of Earthworm Castings Using Solid Fuel Ash

Figure 1:
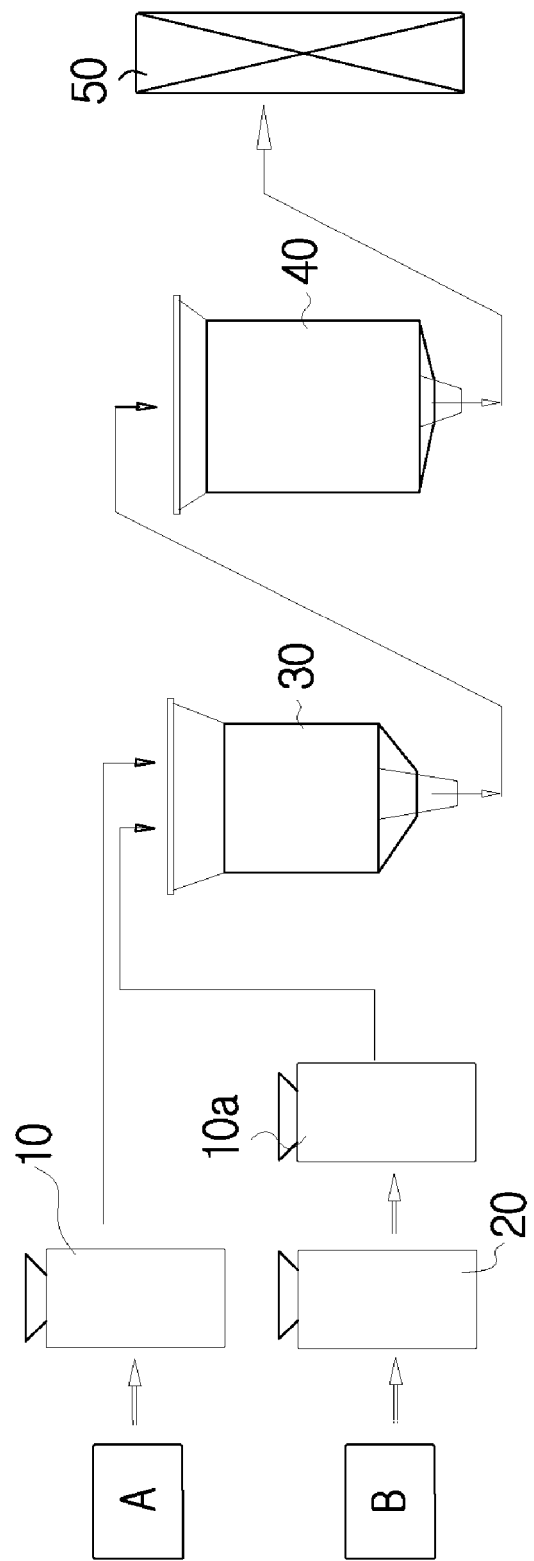
FIG. 1 is a process flow diagram showing a process of preparing earthworm feed according to the present invention.
Figure 2:
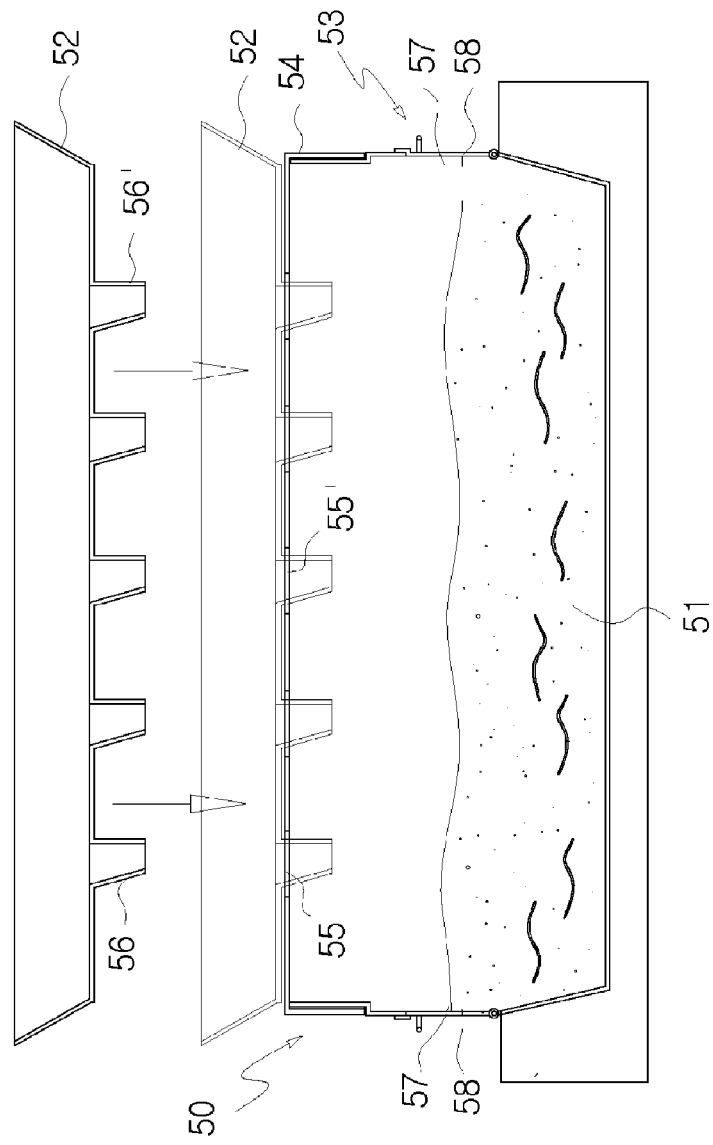
FIG. 2 shows the entire configuration of an earthworm bed according to the present invention.
Figure 3:
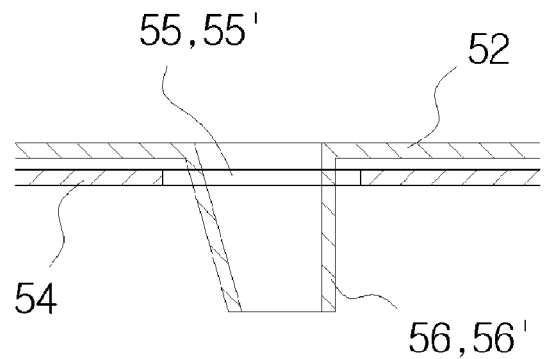
FIG. 3 shows an important part of the earthworm bed shown in FIG. 2.

As shown in FIG. 1, solid fuel ash A which is discharged as powder from a solid fuel boiler and collected together with incomplete ash which is discharged as a mass, and the collected material is ground in a grinding container 10.

The solid fuel ash "A" is ground to a particle size of 0.2-0.5 mm which is slightly larger than the particle size of general yellow earth (0.02-0.05 mm), or it is ground to the same particle size as that of yellow earth, so that it is easily eaten by earthworms.

Meanwhile, shells such as oysters, bloody clams or short-necked clams, and crab shells "B" are washed in a washing container 20 to remove salt from the surface, and 80% or more of water is removed therefrom. The washing and the water removal are carried out to remove salt from the shells and the crab shells, because the salt can be harmful to earthworms.

The washed shells and crab shells "B" are ground in a grinding container 10a. As in the case of the solid fuel ash "A", the shells and crab shells "B" are ground to a particle size of 0.2-0.5 mm which is slightly larger than the particle size of general yellow earth (0.02-0.05 mm), or they are ground to the same particle size as that of yellow earth.

The ground solid fuel "A" and the shells and crab shells "B" are mixed with yellow earth in a mixer 30.

In the mixer 30, 60-70 wt % of yellow earth is mixed with 20-30 wt % of the solid fuel ash and 10-20 wt % of the shells and the crab shells, while water is added thereto so that the mixture has a water content of 70% or higher.

The mixture is transferred from the mixer to a fermenter 40 in which it is then fermented and matured. The maturation of the mixture is performed because earthworms take only somewhat mature feed.

The feed obtained by mixing yellow earth with the solid fuel ash "A." and the shells and the crab shells "B" and maturing the mixture in the fermenter 40 as described above is fed to earthworms in an earthworm bed 50 to allow the earthworms to produce earthworm castings.

Hereinafter, the configuration of the earthworm bed 50 will be described.

Earthworm Bed

The earthworm bed 50 for producing earthworm castings comprises: a feeding unit 52 for giving the feed prepared by mixing the solid fuel ash A, the shells and crab shells B and yellow earth; a breeding chamber 51 in which earthworms are bred to produce earthworm castings; a discharge unit 53 through which the earthworm castings produced in the breeding chamber 51 are discharged.

The breeding chamber 51 is formed in the shape of a box, and a cover 54 is detachably coupled to the top. A plurality of holes 55 and 55' are formed through the cover 54 such that the feed can be fed through the holes 55 and 55'. The holes 55 and 55' of the cover 54 usually allow the breeding chamber 51 to be ventilated, and when the feed is to be fed, the feeding unit is coupled with the holes 55 and 55'.

Feeding pipes 56 and 56' which fit into the holes 55 and 55' of the breeding chamber 51 are formed to extend from the feeding unit 52. Thus, when the feed is to be fed, the feeding pipes 56 and 56' are coupled to the holes 55 and 55', and the feed is fed downward into the breeding chamber 51 through the feeding pipes 56 and 56' of the feeding unit 52.

When water is to be supplied to control the humidity of the breeding chamber 51, the feeding pipes 56 and 56' of the feeding unit 52 are coupled to the holes 55 and 55', and water is supplied through the feeding pipes 56 and 56' to the breeding chamber 51.

Earthworms generally live in the moist soil at a depth of 20 cm or more. Thus, when earthworms are to be placed, soil having a sufficient water content and an optimal humidity is filled in the breeding chamber 51 to a sufficient height, and earthworms are placed thereon, and a thermometer and a hygrometer are provided in the breeding chamber 51 in order to monitor the temperature and humidity of the breeding chamber 51.

Meanwhile, at one side of the breeding chamber 51, a discharge unit 53 for discharging produced earthworm castings is formed. The discharge unit 53 has a discharge opening 57 formed at one side of the breeding chamber 51, and a discharge door 58 is coupled to the discharge opening 57 such that it can be open downward.

The discharge opening 57 is preferably formed higher than level of the soil in which earthworms live, so that the earthworms are not damaged when earthworm castings are discharged.

Figure 4:
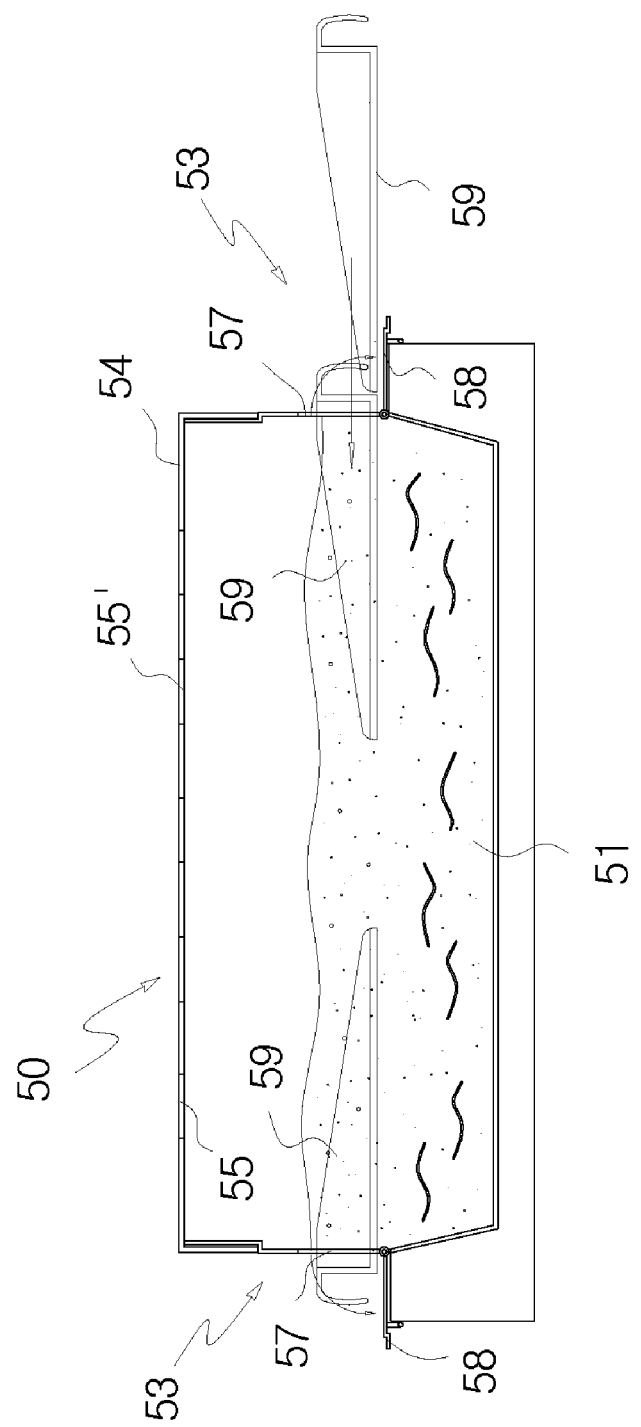
FIG. 4 shows a state in which an earthworm bed according to the present invention is used.

As shown in FIG. 4, when the discharge opening 57 of the discharge door 58 is open, a discharge scoop can be inserted into the breeding chamber 59 such that earthworm castings produced at the upper layer of the breeding chamber can be taken out.

The earthworm castings are not completely discharged from the breeding chamber 51, but about 60% of the earthworm castings are discharged and the remainder can be mixed with the earthworm habitat and fresh feed, whereby good and optimal breeding conditions can always be maintained.

Terms or words used in the specification and the appended claims, including the description of reference numerals, should not be construed as having normal or dictionaric meanings, and should be construed as having meanings and concepts which conform with the technical spirit of the present invention according to a principle that the inventor can properly define the concepts of the terms in order to describe his/her own invention in the best way.

According to the present invention, shells such as oysters, bloody clams or short-necked clams, crab shells, and yellow earth are mixed with ash generated from the combustion of solid fuels, and the mixture is fed to earthworms, whereby problems associated with the disposal of the soil fuel ash can be solved while earthworm castings can be produced using the solid fuel ash.

Solid fuel ash is discharged from a solid fuel boiler in which solid fuel is burned to use the combustion heat thereof. In the process of discharging ash from the solid fuel boiler, powder ash is discharged together with an incomplete ash mass. This incomplete ash mass is ground in the grinding device.

Shells such as oysters, bloody clams or short-necked clams, and crab shells are washed with water to remove salt, and are ground to powder in a state in which they contain the water used in the washing process.

The ground solid fuel ash and the ground shells and crab shells are mixed with yellow earth and transferred into a fermenter in which they are then matured. The matured mixture is fed to earthworms in an earthworm bed to produce earthworm castings.

The earthworm bed for producing earthworm castings comprises: a feeding unit through which feed prepared by mixing solid fuel ash with shell and crab shell powders is fed; a breeding unit in which earthworms are bred to produce earthworm castings; and a discharge unit through which the earthworm castings are discharged.

As described above, according to the present invention, ash from a solid fuel boiler is not disposed and is used as earthworm feed to produce earthworm castings, whereby problems associated with the disposal of solid fuel ash can be solved in an environmentally friendly and economical manner. In addition, earthworm castings produced using the solid fuel ash as feed can be produced into fertilizers, soil amendments.

The invention claimed is:

1. A method for producing earthworm castings, the method comprising the steps of:
   grinding solid fuel ash;
   washing shells and crab shells to remove salt, and then removing 80% or more of water therefrom;
   grinding the washed shells and crab shells;
   mixing 60-70 wt % of yellow earth, 20-30 wt % of the solid fuel ash and 10-20 wt % of the ground shells and crab shells;
   fermenting and maturing the mixture; and
   feeding the matured mixture to earthworms to allow the earthworms to produce earthworm castings.

* * * * *